United States Patent
Yu

(10) Patent No.: US 10,258,463 B2
(45) Date of Patent: Apr. 16, 2019

(54) PHAKIC INTRAOCULAR LENS IMPLANTATION WITHOUT VISCOELASTICS AND INSTRUMENT THEREOF

(71) Applicant: EYE HOSPITAL, WENZHOU MEDICAL UNIVERSITY, Wenzhou, Zhejiang (CN)

(72) Inventor: Ayong Yu, Zhejiang (CN)

(73) Assignee: EYE HOSPITAL, WENZHOU UNIVERSITY, Wenzhou, Zhejiang (CN)

( * ) Notice: Subject to any disclaimer, the term of this patent is extended or adjusted under 35 U.S.C. 154(b) by 219 days.

(21) Appl. No.: 15/280,891

(22) Filed: Sep. 29, 2016

(65) Prior Publication Data

US 2017/0354495 A1  Dec. 14, 2017

(30) Foreign Application Priority Data

Jun. 14, 2016  (CN) .................. 2016 1 04135774
Jun. 14, 2016  (CN) .................. 2016 1 04195597

(51) Int. Cl.
| | |
|---|---|
| A61F 2/16 | (2006.01) |
| A61F 9/00 | (2006.01) |
| A61F 9/007 | (2006.01) |
| A61F 9/01 | (2006.01) |
| A61M 3/02 | (2006.01) |

(52) U.S. Cl.
CPC .......... *A61F 2/1675* (2013.01); *A61F 2/1664* (2013.01); *A61M 3/02* (2013.01); *A61M 3/0279* (2013.01); *A61M 2210/0612* (2013.01)

(58) Field of Classification Search
CPC ... A61F 9/00736; A61F 9/007; A61F 9/00763
USPC ........................................................... 604/294
See application file for complete search history.

(56) References Cited

U.S. PATENT DOCUMENTS

| | | | |
|---|---|---|---|
| 4,331,130 A * | 5/1982 | Lewicky | A61F 9/00736 604/23 |
| 5,755,700 A | 5/1998 | Kritzinger et al. | |
| 5,800,406 A | 9/1998 | Kritzinger et al. | |
| 6,135,984 A * | 10/2000 | Dishler | A61F 9/007 604/181 |

(Continued)

FOREIGN PATENT DOCUMENTS

| | | |
|---|---|---|
| CN | 204521166 U | 8/2015 |
| RU | 2083192 A | 7/1997 |
| WO | WO 2015/144995 A1 | 10/2015 |

*Primary Examiner* — Julian W Woo
(74) *Attorney, Agent, or Firm* — Christensen, Fonder, Dardi & Herbert PLLC

(57) ABSTRACT

A novel phakic intraocular lens implantation without viscoelastics and an instrument thereof. The special designed instrument is employed to achieve a purpose of maintaining an anterior chamber only with a perfusion liquid in the surgery, so as to get rid of the influence of the viscoelastics completely. The viscoelastics are not used, so that there is no need to inject the viscoelastics or remove the viscoelastics as in traditional methods, the surgery time is shortened such that total time of surgical procedures from incision construction to incision hydration can be reduced to only 1~3 minutes, and viscoelastic-related complications, such as postoperative high intraocular pressure and lens opacity, are completely avoided.

17 Claims, 9 Drawing Sheets

(56) References Cited

U.S. PATENT DOCUMENTS

| | | | |
|---|---|---|---|
| 6,695,821 B1 * | 2/2004 | Sjaarda | A61M 3/0279 |
| | | | 604/264 |
| 7,037,296 B2 | 5/2006 | Kadziauskas et al. | |
| 2003/0093099 A1 * | 5/2003 | Anthone | A61F 9/00736 |
| | | | 606/166 |
| 2016/0374854 A1 * | 12/2016 | Nallakrishnan | A61F 9/00736 |
| | | | 604/27 |

* cited by examiner

PHAKIC INTRAOCULAR LENS IMPLANTATION WITHOUT VISCOELASTICS AND INSTRUMENT THEREOF

RELATED APPLICATION

The present application claims priority to Chinese Patent Application No. 2016104195597, filed Jun. 14, 2016, and Chinese Patent Application No. 2016104135774, filed Jun. 14, 2016, the disclosures of which are hereby incorporated by reference herein in their entireties.

TECHNICAL FIELD

The present invention relates to the technical field of intraocular lens surgery in ophthalmology, in particularly to a novel phakic intraocular lens implantation without viscoelastics and an instrument thereof.

BACKGROUND ART

Phakic intraocular lens implantation is a principal method for surgical correction of high myopia, wherein the ICL (Implantable Collamer Lens) is the mainstream phakic intraocular lens at present. About 150 thousand cases are implanted annually in the global, and about 30 thousand cases are implanted annually in China. Although the phakic intraocular lens implantation has achieved giant success clinically, a problem exists in the surgical operation procedures, that is, viscoelastics are needed for maintaining the anterior chamber in the operation, but the viscoelastics between an intraocular lens and a natural lens is difficult to remove completely, which may result in two main complications: 1, high intraocular pressure response in early postoperative period, which usually can be increased within two hours in postoperative period, and if the complication was not recognized or treated timely, ophthalmalgia, blur vision, and even blindness, can be caused due to the drastically increased intraocular pressure; 2, the residual viscoelastics having influence on nutrient metabolism of the lens, or viscoelastic toxicity effect, may result in the lens opacity in early postoperative period, and even a cataract leading to impairment of vision, so that it is necessary to take out the phakic intraocular lens by secondary surgery, and remove the cataract.

To seek for a safe and reliable phakic intraocular lens surgical method is always an effort direction of ophthalmologists. From a view of the present improved situation, there are mainly two strategies: 1. improving the performance and quality of viscoelastics. However, due to a process needing the viscoelastics to maintain the anterior chamber during the surgery process is not changed, the viscoelastics remained between the intraocular lens and the natural lens may still cause postoperative high intraocular pressure response. 2. Reducing the amount of the viscoelastics injected into the anterior chamber as far as possible. However, a small amount of the viscoelastics results in unstable maintenance of the anterior chamber, so that the intraocular lens may graze the natural lens in the implantation, resulting in the lens opacity, even a cataract to impair vision.

SUMMARY OF THE INVENTION

In order to solve the deficiencies in the prior art, the present invention provides a novel phakic intraocular lens implantation without viscoelastics and an instrument thereof. The mindset of thinking that viscoelastics are needed for maintaining an anterior chamber in the phakic intraocular lens implantation is broken through, and the special designed instrument is employed to achieve a purpose of maintaining the anterior chamber only with an irrigation liquid in the surgery, so as to get rid of the influence of the viscoelastics completely.

The technical solution employed by the present invention is as follows: a novel phakic intraocular lens implantation without viscoelastics, characterized by comprising the following steps:

1. performing sterilization and draping for an operation eye, placing an eye speculum, and washing a conjunctival sac;
2. loading an intraocular lens into a loader;
3. according to directions of watch hands, at the corneal limbus in the 6 and 12 o'clock directions, and parallel to iris directions, passing through an irrigation incision with a dimension of 0.6×0.5 mm constructed with an irrigation maintainer corneal stab knife and passing through a position adjusting incision with a dimension of 0.2×0.5 mm constructed with a position adjustor corneal stab knife;
4. inserting a specially made anterior chamber irrigation maintainer through the irrigation incision, irrigating the anterior chamber, and maintaining the anterior chamber;
5. constructing a corneal main incision with a dimension of 2.8×1.5 mm at the temporal side;
6. implanting the intraocular lens through the corneal main incision;
7. inserting the position adjustor through the position adjusting incision, and adjusting the position of the intraocular lens;
8. performing incision hydration, and forming the anterior chamber, that is, completing the phakic intraocular lens implantation of the present invention.

The anterior chamber irrigation maintainer comprises an infusion set joint, a catheter with the top end closed is arranged on the infusion set joint, the catheter is made from metal materials, the catheter comprises a straight tube connected with the infusion set joint and a branch tube upwards folded to form an included angle with the straight tube, the front end of the branch tube is an irrigation head, two irrigation holes disposed symmetrically are formed in the side wall of the irrigation head, a through hole is formed between the symmetrically disposed irrigation holes, and an axis of the through hole and an axis of the branch tube are distributed perpendicularly.

The length of the straight tube is 12 mm, the length of the branch tube is 10 mm, and the included angle between the straight tube and the branch tube is 130°.

The top of the irrigation head is arc-shaped, a spherical hollow cavity is formed in the top of the arc-shaped irrigation head, and the spherical center of the spherical hollow cavity within the irrigation head is located at the top of the through hole.

The diameter of the through hole is 0.34 mm.

The diameter of the catheter is 0.5 mm.

The anterior chamber irrigation maintainer corneal stab knife comprises a first handle and a first blade, wherein a first connecting portion is arranged at the front end of the first handle, and the first blade is mounted on the first connecting portion.

The head of the first blade is provided with a first blade edge, and an included angle of 110° is formed between the first blade edge and the first blade.

The front end of the first blade edge is a first cutting tip, the first cutting tip is a regular triangle with a vertex angle of 60°, the length of the first cutting tip is 0.68 mm, and the width is 0.79 mm.

The length of the first blade edge is 10 mm, and the length of the first blade is 17 mm.

A frosted layer for increasing hand-held friction force is arranged on the first handle.

The position adjustor comprises a handle, a position adjusting hook is arranged at the front end of the handle, the position adjusting hook comprises a body connected with the handle and an adjusting head arranged on the body, an included angle is formed between the adjusting head and the body, the top of the adjusting head is hemispherical, and a frosted surface is arranged on the lower hemispherical surface of the top of the hemispherical adjusting head.

The lower side of the adjusting head is an inwards-concave arc, the radius of curvature of the arc of the adjusting head is 5 cm, and the radian of the arc of the adjusting head is π/12.

The diameter of the top of the hemispherical adjusting head is 0.2 mm, and the length of the frosted surface is 0.3 mm.

The length of the body is 17 mm, the diameter is 0.8 mm, and the length of the adjusting head is 12 mm.

An included angle of 110° is formed between the adjusting head and the body.

The position adjustor corneal stab knife comprises a second handle and a second blade, wherein a second connecting portion is arranged at the front end of the second handle, and the second blade is mounted on the second connecting portion.

The head of the second blade is provided with a second blade edge, and an included angle of 110° is formed between the second blade edge and the second blade.

The front end of the second blade edge is a second cutting tip, the second cutting tip is a right angled triangle with a vertex angle of 15°, the length of the second cutting tip is 0.77 mm, and the width is 0.2 mm.

The length of the second blade edge is 10 mm, and the length of the second blade is 17 mm.

The beneficial effects of the present invention are as follows: the present invention provides a novel phakic intraocular lens implantation without viscoelastics and an instrument thereof. The special designed instrument is employed to achieve a purpose of maintaining an anterior chamber only with an irrigation liquid in the surgery, so as to get rid of the influence of the viscoelastics completely. The viscoelastics are not used, so that there is no need to inject the viscoelastics or remove the viscoelastics as traditional methods, the surgery time is shortened obviously, total time of surgical procedures from incision construction to incision hydration can be reduced to only 1~3 minutes, and viscoelastic-related complications, such as postoperative high intraocular pressure and lens opacity, are completely avoided. The novel surgical method provides new thinking for intraocular lens surgery, and can obviously improve the clinical safety of the phakic intraocular lens surgery.

In the figures: 11—infusion set joint, 12—catheter, 13—first handle, 14—first blade, 121—straight tube, 122—branch tube, 123—irrigation head, 124—irrigation hole, 125—through hole, 131—first connecting portion, 132—frosted layer, 141—first blade edge, 142—first cutting tip, 21—handle, 22—position adjusting hook, 23—second handle, 24—second blade, 221—adjusting head, 222—frosted surface, 231—second connecting portion, 241—second blade edge, 242—second cutting tip.

DETAILED DESCRIPTION OF THE INVENTION

Figure 1:
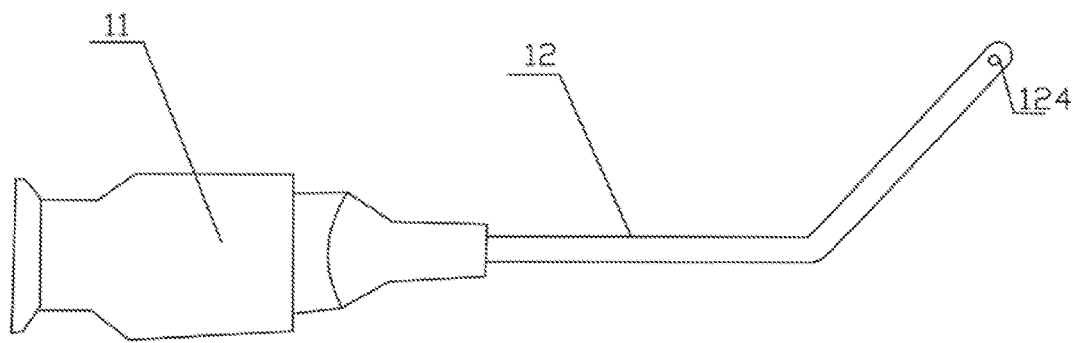
FIG. 1 is a structural diagram of an anterior chamber irrigation maintainer provided by the present invention.
Figure 2:
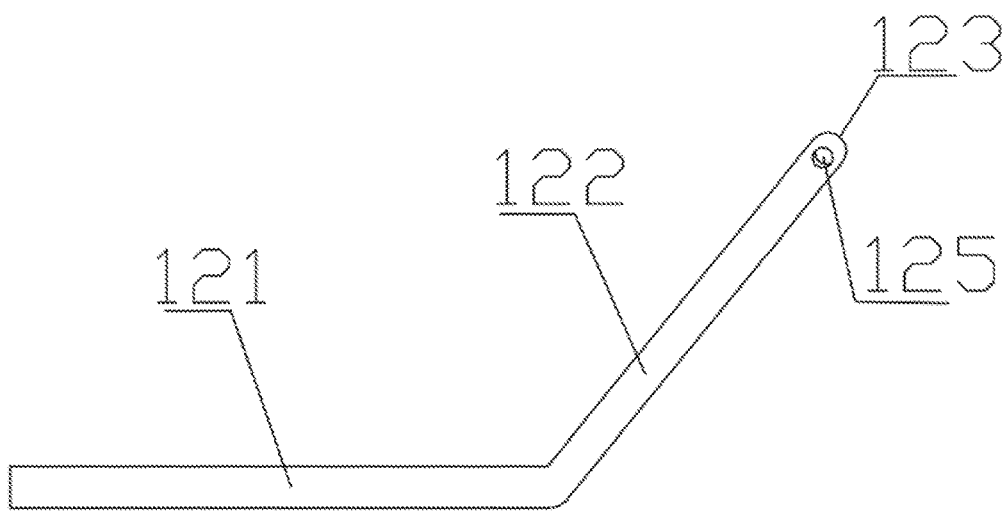
FIG. 2 is an enlarged structural diagram of a catheter of the anterior chamber irrigation maintainer provided by the present invention.
Figure 3:
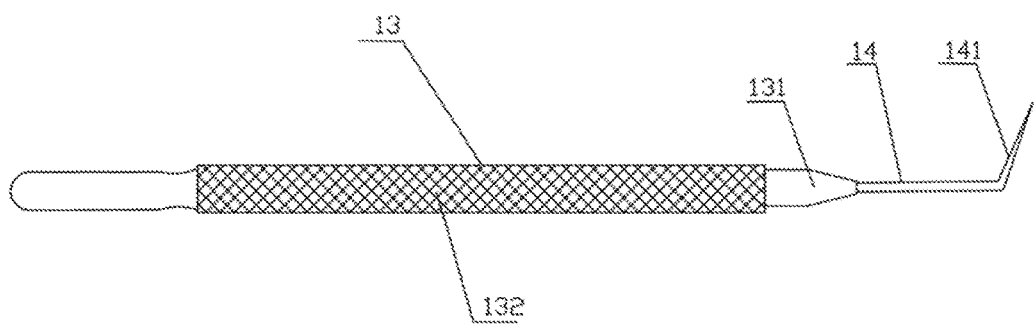
FIG. 3 is a structural diagram of a corneal stab knife provided by the present invention.
Figure 4:
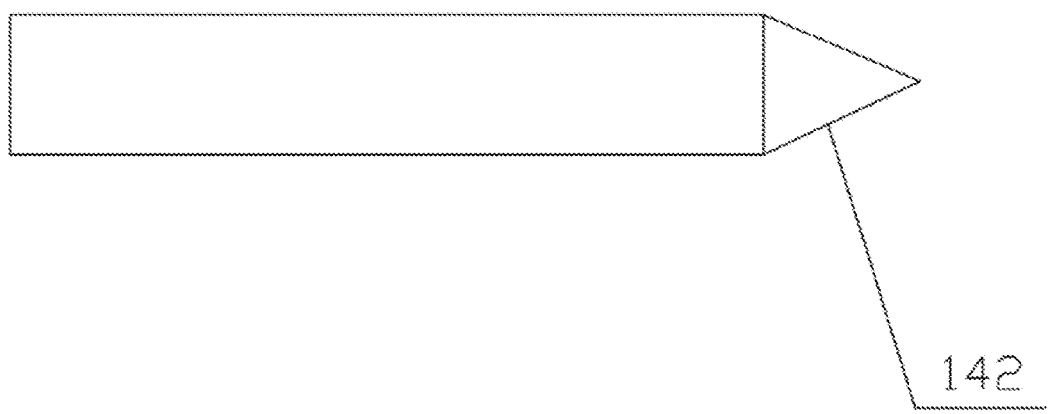
FIG. 4 is an enlarged structural diagram of a cutting tip of the corneal stab knife provided by the present invention.
Figure 5:
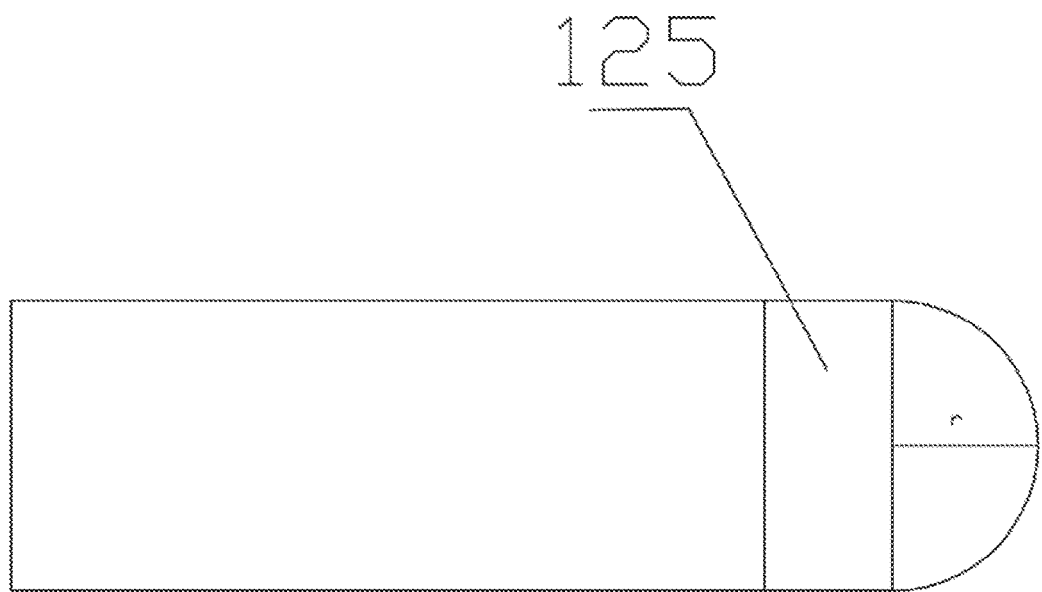
FIG. 5 is a structural sectional view of the catheter of the anterior chamber irrigation maintainer provided by the present invention.
Figures 6A, 6B:
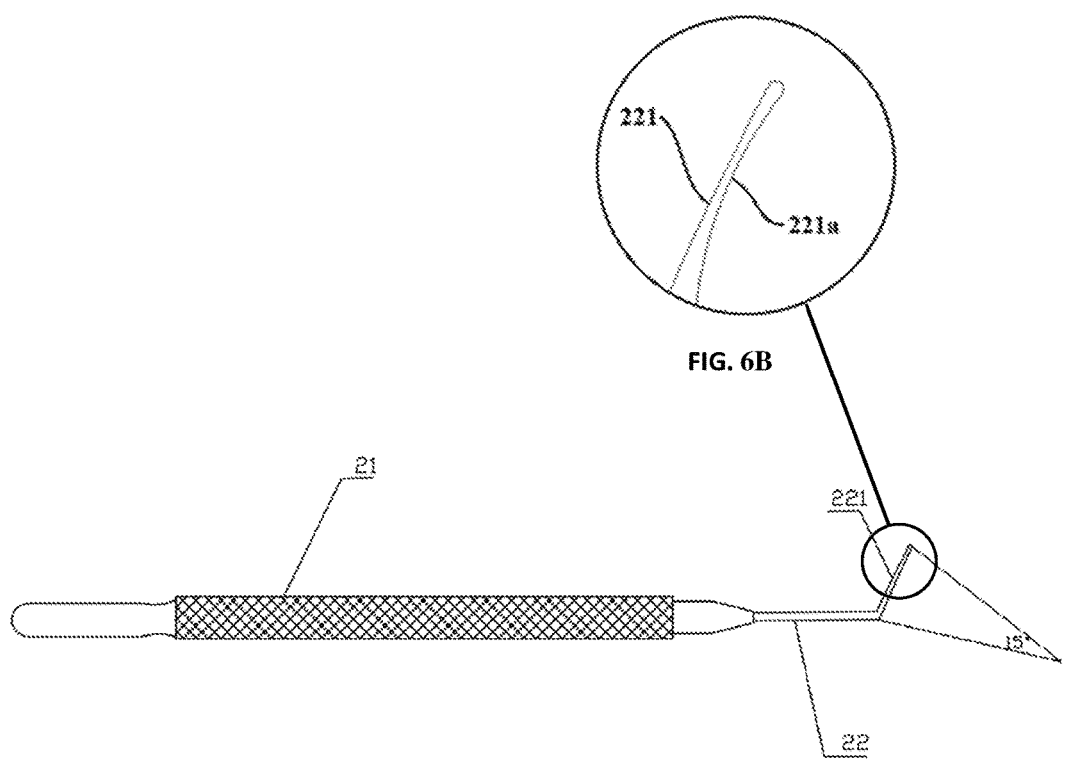
FIG. 6A is a structural diagram of a position adjustor of the phakic intraocular lens provided by the present invention.
FIG. 6B is a detailed view of the adjusting head of FIG. 6A.
Figure 7:
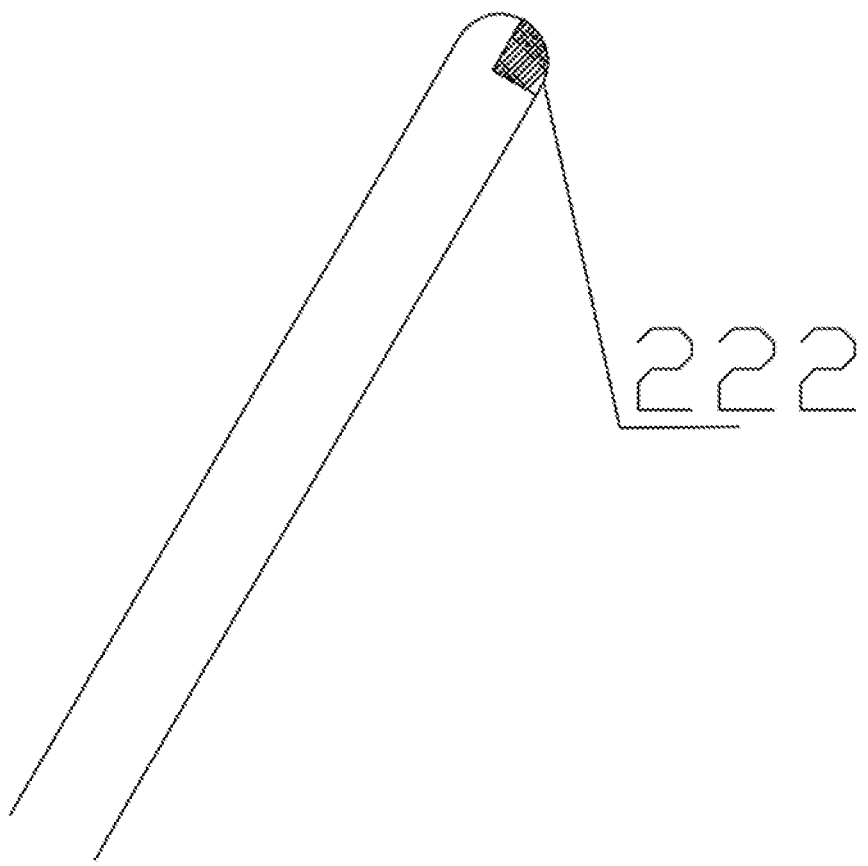
FIG. 7 is an enlarged structure diagram of an adjusting head of the position adjustor of the phakic intraocular lens provided by the present invention.
Figure 8:
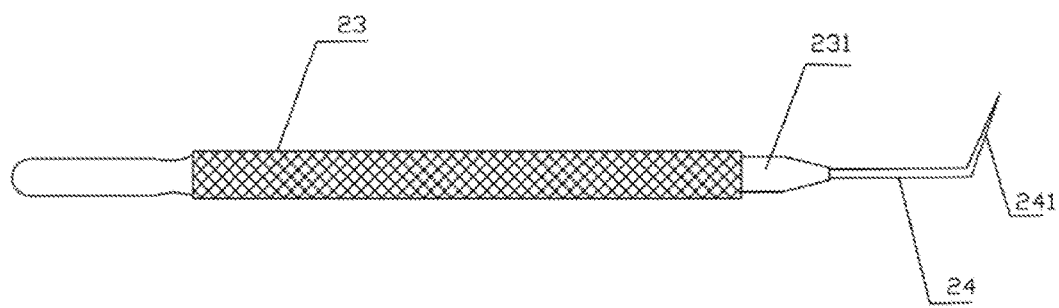
FIG. 8 is a structural diagram of the corneal stab knife provided by the present invention.
Figure 9:
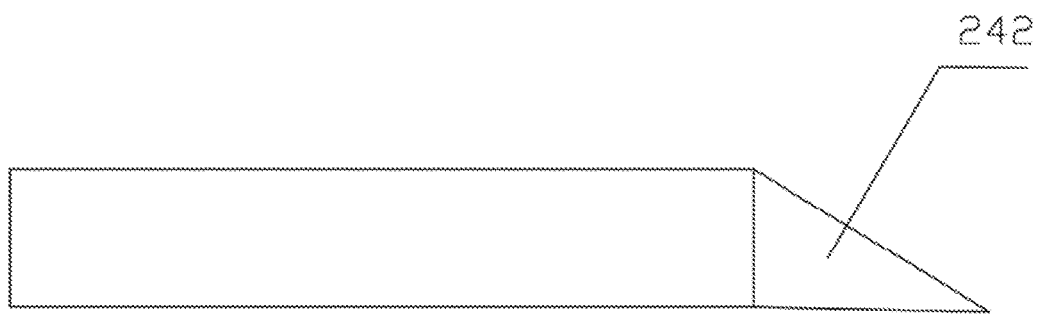
FIG. 9 is an enlarged structural diagram of the cutting tip of the corneal stab knife provided by the present invention.

The present invention is further described in combination with FIG. 1, FIG. 2, FIG. 3, FIG. 4, FIG. 5, FIG. 6A, FIG. 6B, FIG. 7, FIG. 8 and FIG. 9. A novel non-viscoelastics phakic intraocular lens implantation comprises the following steps:

(1) performing sterilization and draping for an operation eye, placing an eye speculum, and washing a conjunctival sac;

(2) loading an intraocular lens into a loader;

(3) according to directions of watch hands, at the corneal limbus in the 6 and 12 o'clock directions, and parallel to iris directions, passing through an irrigation incision with a dimension of 0.6×0.5 mm constructed with an irrigation maintainer corneal stab knife and passing through a position adjusting incision with a dimension of 0.2×0.5 mm constructed with a position adjustor corneal stab knife;

(4) inserting a specially made anterior chamber irrigation maintainer through the irrigation incision, irrigating the anterior chamber, and maintaining the anterior chamber;

(5) constructing a corneal main incision with a dimension of 2.8×1.5 mm at the temporal side;

(6) implanting the intraocular lens through the corneal main incision;

(7) inserting the position adjustor through the position adjusting incision, and adjusting the position of the intraocular lens;

(8) performing incision hydration, and forming the anterior chamber, that is, completing the phakic intraocular lens implantation of the present invention.

The present invention has broken through the mindset of thinking that viscoelastics are needed for maintaining an anterior chamber in the phakic intraocular lens implantation, and the special designed instrument is employed to achieve a purpose of maintaining the anterior chamber only with an irrigation liquid in the surgery, so as to get rid of the influence of the viscoelastics completely. 35 cases of phakic intraocular lens implantation were carried out by adopting the method at the early stage, and were completed successfully. Through observation, it finds that a significant improvement effect is obtained. The intraocular pressure before surgery, and the intraocular pressure within two hours, 1 day, 1 week in postoperative period are 14.22±2.59 (7.7~19.1), 16.59±3.79 (13.6~25.2), 13.00~12.90 (11.7~20.6), 14.11±1.93 (12.9~17.7) mmHg, respectively; no high intraocular pressure requiring medical intervention appears within 2 hours in postoperative period; the intraocular pressure is all in the normal range within 1 day in postoperative period. It should be noted that the method has the additional advantage of obviously shortened surgical time, because there is no need to inject the viscoelastics or remove the viscoelastics as traditional methods, and total time of surgical procedures from incision construction to incision hydration can be reduced to only 1~3 minutes. The above results have shown that the surgical method is effective and feasible in patients with phakic intraocular lens implantation.

The anterior chamber irrigation maintainer comprises an infusion set joint 11, wherein a catheter 12 with the top end closed is arranged on the infusion set joint 11 and the catheter 12 is made from metal materials. The catheter 12 comprises a straight tube 121 connected with the infusion set joint 11 and a branch tube 122 upwards folded to form an included angle with the straight tube 121. The front end of the branch tube 122 is an irrigation head 123, and two irrigation holes 124 disposed symmetrically are formed in the side wall of the irrigation head 123. A through hole 125 is formed between the symmetrically disposed irrigation holes 124, and an axis of the through hole 125 and an axis of the branch tube 122 are distributed perpendicularly. By providing the two symmetrically disposed irrigation holes in the side wall of the irrigation head of the anterior chamber irrigation maintainer, whirls produced within the anterior chamber during irrigation are balanced, the impact on eye tissue is further reduced, irrigation can be performed through a fine incision to enter the anterior chamber, and the stable anterior chamber is maintained, so that therein is no need to add viscoelastics in the anterior chamber, and viscoelastics related operation steps and time, potential risks of complications, as well as costs associated are avoided. After a water flow enters the hemispherical spherical hollow cavity, the water flow flows out from the through hole after mutual reflux force offsets each other, thereby retarding the impact of the water flow, balancing the whirls produced within the anterior chamber during irrigation, and further reducing the impact on the eye tissue. Moreover, a hollow cavity is arranged in the top of the arc-shaped irrigation head 123, so that the irrigation water flow will first enter the hollow cavity at the top of the irrigation head 123, then flow back, and flow out through the two symmetrically disposed irrigation holes 124, and the impact force is retarded.

The length of the straight tube 121 is 12 mm, the length of the branch tube 122 is 10 mm, and the included angle between the straight tube 121 and the branch tube 122 is 130°. The top of the irrigation head 123 is arc-shaped, a spherical hollow cavity is arranged in the top of the arc-shaped irrigation head 123, and the spherical center of the spherical hollow cavity in the irrigation head 123 is located at the top of the through hole 125.

The diameter of the through hole 125 is 0.34 mm.

The diameter of the catheter 12 is 0.5 mm.

The anterior chamber irrigation maintainer corneal stab knife comprises a first handle 13 and a first blade 14, wherein a first connecting portion 131 is arranged at the front end of the first handle 13, and the first blade 14 is mounted on the first connecting portion 131. The head of the first blade 14 is provided with a first blade edge 141, and an included angle of 110° is formed between the first blade edge 141 and the first blade 14. The front end of the first blade edge 141 is a first cutting tip 142, the first cutting tip 142 is a regular triangle with a vertex angle of 60°, the length of the first cutting tip 142 is 0.68 mm, and the width is 0.79 mm. The length of the first blade edge 141 is 10 mm, and the length of the first blade 14 is 17 mm. A frosted layer 132 for increasing hand-held friction force is arranged on the first handle 13. According to the invention, a blade with a small diameter is employed, and can construct a fine incision matched with the anterior chamber irrigation instrument, thereby not only shortening the length of the blade edge entering the anterior chamber and improving the safety, but also reducing the water leakage of the incision to maintain stable anterior chamber. The dependence on the operator's experience is reduced. At the same time, the length of the top end of the blade edge is short, which can avoid related accidental hurt.

The position adjustor comprises a handle 21, wherein a position adjusting hook 22 is arranged at the front end of the handle 21, the position adjusting hook 22 comprises a body connected with the handle 21 and an adjusting head 221 arranged on the body, an included angle is formed between the adjusting head 221 and the body, the top of the adjusting head 221 is hemispherical, and a frosted surface 222 is arranged on the lower hemispherical surface of the top of the hemispherical adjusting head 221. According to the invention, the bottom of the top of the adjusting head 221 is subjected to sanding treatment, so that the instrument goes in and out of the incisions conveniently, and the increase in contact force during position adjustment is facilitated, and position adjustment is enabled to be convenient and fast. According to the invention, small diameter and frosted bottom at the top portion and are adopted, the position adjustor can enter the anterior chamber with a 0.2 mm fine incision to adjust the position of the phakic intraocular lens. In the operation process, the anterior chamber is stable and the position is adjusted conveniently, and disadvantages of big incisions and difficulty in position adjustment of traditional position adjusting instrument are avoided.

The lower side 221a of the adjusting head 221 is an inwards-concave arc, the radius of curvature of the arc of the adjusting head 221 is 5 cm, and the radian of the arc of the adjusting head 221 is $\pi/12$.

The diameter of the top of the hemispherical adjusting head 221 is 0.2 mm, and the length of the frosted surface 222 is 0.3 mm.

The length of the body is 17 mm, the diameter is 0.8 mm, and the length of the adjusting head 221 is 12 mm.

An included angle of 110° is formed between the adjusting head 221 and the body.

The position adjustor corneal stab knife comprises a second handle 23 and a second blade 24, wherein a second connecting portion 231 is arranged at the front end of the second handle 23, and the second blade 24 is mounted on the second connecting portion 231. The head of the second blade 24 is provided with a second blade edge 241, and an included angle of 110° is formed between the second blade edge 241 and the second blade 24. The front end of the second blade edge 241 is a second cutting tip 242, the second cutting tip 242 is a right angled triangle with a vertex angle of 15°, the length of the second cutting tip 242 is 0.77 mm, and the width is 0.2 mm. The length of the second blade edge 241 is 10 mm, the length of the second blade 24 is 17 mm. A blade with a small diameter is employed, and can construct a fine incision matched with the anterior chamber irrigation instrument, thereby not only shortening the length of the blade edge entering the anterior chamber and improving the safety, but also reducing the water leakage of the incision to maintain stable anterior chamber.

The described above is only the preferred embodiments of the present invention, but the protection scope of the present invention is not limited to the above embodiments, and all of technical solutions belonging to the idea of the present invention are within the protection scope of the present invention. To the ordinary skilled in the technical field, it should be noted that the improvements and the modifications not departing from the principle of the invention shall be considered to be within the protection range of the invention.

The invention claimed is:

1. A phakic intraocular lens implantation method without viscoelastics, comprising the following steps:
   (1) performing sterilization and draping for an eye that is to be operated on, placing an eye speculum on the eye, and washing a conjunctival sac;
   (2) loading an intraocular lens into a loader;
   (3) at the corneal limbus of the eye, and parallel to iris directions, passing through an irrigation incision constructed with an irrigation maintainer corneal stab knife and passing through a position adjusting incision constructed with a position adjustor corneal stab knife;
   (4) inserting an anterior chamber irrigation maintainer through the irrigation incision into an anterior chamber of the eye, irrigating the anterior chamber with irrigation liquid, and maintaining the anterior chamber with the irrigation liquid via the anterior chamber irrigation maintainer;
   (5) constructing a corneal main incision at a temporal side of the eye;
   (6) implanting the intraocular lens through the corneal main incision;
   (7) inserting a position adjustor through the position adjusting incision, and adjusting the position of the intraocular lens;
   (8) performing incision hydration, thereby completing the phakic intraocular lens implantation;
   wherein the position adjustor according to step (7) comprises a handle, wherein a position adjusting hook is arranged at the front end of the handle, the position adjusting hook comprises a body connected with the handle and an adjusting head arranged on the body, an included angle is formed between the adjusting head and the body, the top of the adjusting head is hemispherical, and a frosted surface is arranged on the lower hemispherical surface of the top of the hemispherical adjusting head;
   and wherein the anterior chamber irrigation maintainer, comprises an infusion set joint and a catheter with a closed top end which is arranged on the infusion set joint, the catheter is made from metal materials, the catheter comprises a straight tube connected with the infusion set joint and a branch tube upwardly folded to form an included angle with the straight tube, the front end of the branch tube is an irrigation head, two irrigation holes disposed symmetrically are formed in a side wall of the irrigation head, a through hole is formed between the symmetrically disposed irrigation holes, and an axis of the through hole and an axis of the branch tube are distributed perpendicularly, wherein a top of the irrigation head is arc-shaped, a spherical cavity is formed in the top of the arc-shaped irrigation head, and a spherical center of the spherical cavity within the irrigation head is located at a top of the through hole.

2. The phakic intraocular lens implantation method without viscoelastics according to claim 1, wherein a length of the straight tube is 12 mm, a length of the branch tube is 10 mm, and the included angle between the straight tube and the branch tube is 130°.

3. The phakic intraocular lens implantation method without viscoelastics according to claim 1, wherein a diameter of the through hole is 0.34 mm.

4. The phakic intraocular lens implantation method without viscoelastics according to claim 1, wherein a diameter of the catheter is 0.5 mm.

5. The phakic intraocular lens implantation method without viscoelastics according to claim 1, wherein the anterior irrigation maintainer corneal stab knife comprises a first handle and a first blade, a first connecting portion is arranged at the front end of the first handle, and the first blade is mounted on the first connecting portion.

6. The phakic intraocular lens implantation method without viscoelastics according to claim 5, wherein a first blade edge is arranged at the head of the first blade, and an included angle of 110° is formed between the first blade edge and the first blade.

7. The phakic intraocular lens implantation method without viscoelastics according to claim 6, wherein the front end of the first blade edge is a first cutting tip, the first cutting tip is a regular triangle with a vertex angle of 60°, the length of the first cutting tip is 0.68 mm, and the width is 0.79 mm.

8. The phakic intraocular lens implantation method without viscoelastics according to claim 6, wherein the length of the first blade edge is 10 mm, and the length of the first blade is 17 mm.

9. The phakic intraocular lens implantation method without viscoelastics according to claim 1, wherein the position adjustor corneal stab knife comprises a second handle and a second blade, a second connecting portion is arranged at the front end of the second handle is provided with, and the second blade is mounted on the second connecting portion.

10. The phakic intraocular lens implantation method without viscoelastics according to claim 9, wherein a second blade edge is arranged at the head of the second blade (24), and an included angle of 110° is formed between the second blade edge and the second blade.

11. The phakic intraocular lens implantation method without viscoelastics according to claim 10, wherein the length of the second blade edge is 10 mm, and the length of the second blade is 17 mm.

12. The phakic intraocular lens implantation method without viscoelastics according to claim 10, wherein the front end of the second blade edge is a second cutting tip, the second cutting tip is a right angled triangle with a vertex angle of 15°, the length of the second cutting tip is 0.77 mm, and the width is 0.2 mm.

13. The phakic intraocular lens implantation method without viscoelastics according to claim 1, wherein a lower side of the adjusting head is an inwards-concave arc, the radius of curvature of the arc of the adjusting head is 5 cm, and the radian of the arc of the adjusting head is $\pi/12$.

14. The phakic intraocular lens implantation method without viscoelastics according to claim 1, wherein the diameter of the top of the hemispherical adjusting head is 0.2 mm, and the length of the frosted surface is 0.3 mm.

15. The phakic intraocular lens implantation method without viscoelastics according to claim 1, wherein the length of the body is 17 mm, the diameter is 0.8 mm, and the length of the adjusting head is 12 mm.

16. The phakic intraocular lens implantation method without viscoelastics according to claim 1, wherein an included angle of 110° is formed between the adjusting head and the body.

17. A phakic intraocular lens implantation method without viscoelastics, comprising the following steps:
(1) performing sterilization and draping for an eye that is to be operated on, placing an eye speculum on the eye, and washing a conjunctival sac;
(2) loading an intraocular lens into a loader;
(3) at the corneal limbus of the eye, and parallel to an iris directions, passing through an irrigation incision constructed with an irrigation maintainer corneal stab knife and passing through a position adjusting incision constructed with a position adjustor corneal stab knife;
(4) inserting an anterior chamber irrigation maintainer through the irrigation incision into an anterior chamber of the eye, irrigating the anterior chamber with irrigation liquid, and maintaining the anterior chamber with the irrigation liquid via the anterior chamber irrigation maintainer;
(5) constructing a corneal main incision at a temporal side of the eye;
(6) implanting the intraocular lens through the corneal main incision;
(7) inserting a position adjustor through the position adjusting incision, and adjusting the position of the intraocular lens;
(8) performing incision hydration, thereby completing the phakic intraocular lens implantation.

\* \* \* \* \*